(12) United States Patent
Juarez et al.

(10) Patent No.: US 11,718,839 B1
(45) Date of Patent: Aug. 8, 2023

(54) COMPOSITIONS AND METHODS FOR DEACTIVATING ENVELOPED VIRUSES SUCH AS SARS-COV-2

(71) Applicants: Oscar Juarez, Buffalo Grove, IL (US); Karina Tuz, Buffalo Grove, IL (US); David Do Le Minh, Mokena, IL (US)

(72) Inventors: Oscar Juarez, Buffalo Grove, IL (US); Karina Tuz, Buffalo Grove, IL (US); David Do Le Minh, Mokena, IL (US)

(73) Assignee: ILLINOIS INSTITUTE OF TECHNOLOGY, Chicago, IL (US)

( * ) Notice: Subject to any disclaimer, the term of this patent is extended or adjusted under 35 U.S.C. 154(b) by 158 days.

(21) Appl. No.: 17/378,358

(22) Filed: Jul. 16, 2021

Related U.S. Application Data

(60) Provisional application No. 63/052,779, filed on Jul. 16, 2020.

(51) Int. Cl.
*C12N 9/24* (2006.01)
*C07K 14/705* (2006.01)
*A61K 38/00* (2006.01)

(52) U.S. Cl.
CPC .............. *C12N 9/24* (2013.01); *C07K 14/705* (2013.01); *A61K 38/00* (2013.01); *C07K 2319/00* (2013.01)

(58) Field of Classification Search
None
See application file for complete search history.

(56) References Cited

PUBLICATIONS

Structure-guided glyco-engineering of ACE2 for improved potency as soluble SARS-CoV-2 decoy receptor Tümay Capraz (Year: 2021).*

* cited by examiner

*Primary Examiner* — Kagnew H Gebreyesus
(74) *Attorney, Agent, or Firm* — Pauley Erickson & Swanson

(57) ABSTRACT

A composition and method for preventing and treating infections caused by enveloped viruses, such as SARS-CoV-2 virus. The invention includes compounds having a catalytic domain of a glycosidase and a binding domain that binds the compound to the surface of the targeted virus. The invention also includes a pharmaceutical formulation comprising the compound and a pharmaceutically acceptable carrier to deliver the active portion of the compound to the infecting virus within an infected human or animal. The pharmaceutical formulation can be an inhalant or a nasal spray to the infected human or animal. The invention also includes methods of using a glycosidase or the catalytic part of a glycosidase to deactivate enveloped virus by removing glycans from the viral surface protein.

17 Claims, 6 Drawing Sheets

FIG. 3

FIG. 4A

Figure 1A:
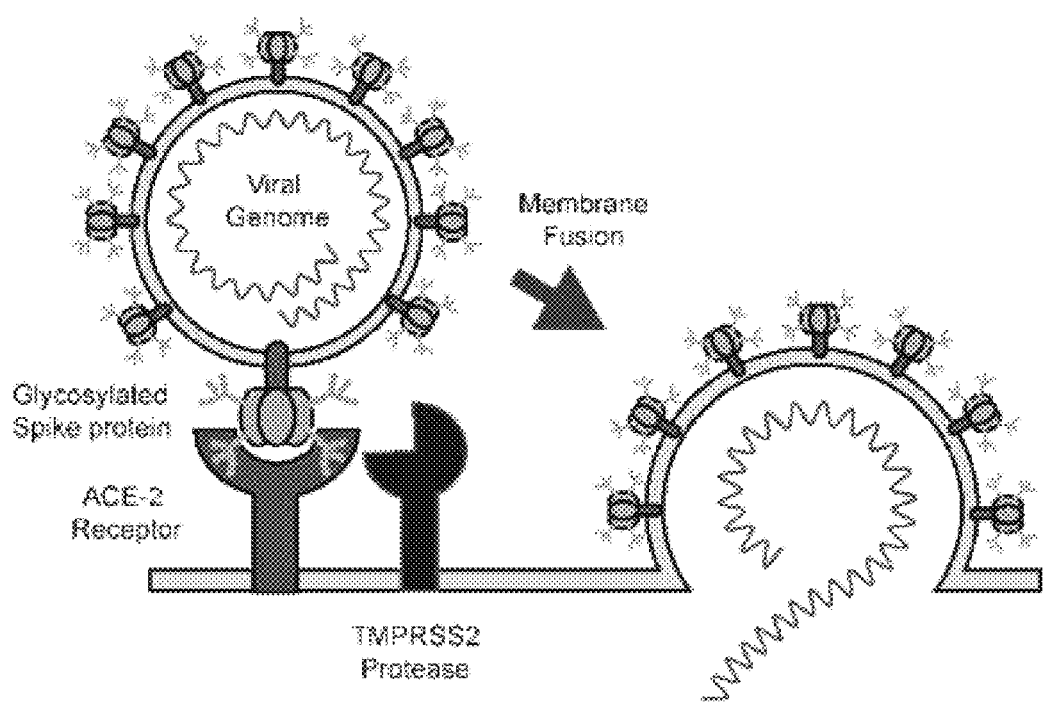

COMPOSITIONS AND METHODS FOR DEACTIVATING ENVELOPED VIRUSES SUCH AS SARS-COV-2

CROSS REFERENCE TO RELATED APPLICATION

This application claims the benefit of U.S. Provisional Patent Application, Ser. No. 63/052,779, filed on Jul. 16, 2020. The provisional application is hereby incorporated by reference herein in its entirely and is made a part hereof, including but not limited to those portions which specifically appear hereinafter.

FIELD OF THE INVENTION

This invention relates generally to therapeutic methods and compositions for treating and/or preventing viral infections in humans and animals, and more specifically, to protein-based therapeutic methods and compositions for treating and/or preventing infection caused by the SARS-CoV-2 virus.

BACKGROUND OF THE INVENTION

The current pandemic produced by the SARS-CoV-2 virus, the causal agent of COVID-19, has compromised the global healthcare system. Enormous efforts at a global scale are being made to produce new antiviral compounds, to repurpose FDA-approved drugs, and to obtain new vaccines that can be used to treat this disease. However, traditional methods to treat infectious diseases have serious limitations, mostly due to the highly evolution and recombination rates of viruses. For instance, the antivirals developed against a single strain of the virus are expected to decrease in effectiveness as new strains appear, which might require complete reformulation. Moreover, as these strains appear, vaccines may only partially protect against the disease or could become completely infective, as had been reported in the case of seasonal vaccines against the common flu. Furthermore, the development of new drugs is time-consuming, extremely expensive, and it is difficult to predict if the outcome would be positive.

In contrast to targeting virus-dependent processes, human-derived processes are attractive alternatives, as the human enzymes would not mutate in a time frame that would allow viruses to become resistant. The "Spike" protein of SARS-CoV-2 coronavirus, responsible for the attachment to the host receptor and the fusion of the viral envelope with the host cell membrane, is heavily N-glycosylated by the host, which helps the virus evade the immune system and infect human cells. There is an urgent need for developing new compositions and treatment to inactivate SARS-CoV-2 coronavirus by impeding the virus invading mechanism to host cells.

SUMMARY OF THE INVENTION

The invention provides new compositions and methods for preventing and treating virus infection, in particular, for treating the SARS-CoV-2 virus which has caused the COVID-19 pandemic.

The invention includes a pharmaceutical formulation for inactivating a virus having fully or partially glycosylated surface glycoproteins. The pharmaceutical formulation includes at least an active portion of a glycosidase and a pharmaceutically acceptable carrier configured to deliver the active portion to an infecting virus within an infected human or animal. The active portion retains enzymatic activity and is adapted to remove glycans from the surface glycoproteins. Exemplary glycosidase is selected from the group consisting of endo- and exo-glycosidases, including: peptide N-glycosidase (PNGase), endo-beta-N-acetylglucosaminidase (ENGase), fucosidase, mannosidase, sialidase, alpha- or beta-galactosidase, neuraminidase, hexosaminidase, aspartyl-glucosaminidase and combinations thereof. In embodiments of this invention, the active portion of the glycosidase is bound to a binding domain corresponding to the surface glycoprotein of the virus. The connecting domain can connect to the active portion and the binding domain.

Embodiments of the invention include compounds having a therapeutic domain, a binding domain, and a connecting domain. The therapeutic domain comprises of an inhibitory activity that prevents or impedes the infection of a virus. The therapeutic domain includes a glycosidase or at least one catalytic domain of a glycosidase. Again, exemplary glycosidases include isoforms of endo- and exo-glycosidases, including: peptide N-glycosidase (PNGase), endo-beta-N-acetylglucosaminidase (ENGase), fucosidase, mannosidase, sialidase, alpha- or beta-galactosidase, neuraminidase, hexosaminidase, aspartyl-glucosaminidase and combinations thereof.

The binding domain binds the therapeutic domain described above to the surface protein of targeted virus. Examples of such a binding domain include the angiotensin-converting enzyme 2 (ACE2) receptor or a soluble domain of the ACE2 receptor, preferably being substantially homologous to human ACE2 receptor. The connecting domain connects the therapeutic and binding domains, increasing contact between the therapeutic domains and targeted virus proteins.

Embodiments of this invention further include an affinity-enhancing domain, which is configured to bind tightly to complex glycans and enhance a catalytic effect of the catalytic domain.

In one aspect, the invention provides a fusion protein for preventing and treating virus infection. One example of such fusion protein is referred to as "CROWNase" herein, which comprises parts of the human PNGase in the therapeutic domain and comprises ACE2 receptor in the binding domain.

In another aspect, the invention includes a glycosidase or an active portion of a glycosidase. Embodiments of the invention include the catalytic domain of a glycosidase but otherwise less than the entire glycosidase sequence. Such embodiments can include other protein sequences such as functional domains derived from other proteins. Certain mutations can be engineered to enhance the catalytic and therapeutic functions of the proteins.

Embodiments of the invention further include a pharmaceutical formulation including said compounds and a pharmaceutically acceptable carrier configured to deliver the active portion of the compound to an infecting virus within an infected human or animal. The pharmaceutical formulation can be formulated in different forms, including nasal sprays, inhalants, tablets, suspensions, solutions for injection or for oral administration, and drops or ointment for eyes. Preferred embodiments of the invention for treating and preventing SARS-CoV-2 are in the formulations of a spray or an inhalant.

Embodiments of the invention also include methods of using a glycosidase or an active portion of a glycosidase to remove glycans from a viral surface protein, comprising contacting the compounds including such glycosidase or the active portion of the glycosidase with the targeted viral surface proteins.

Figure 1B:
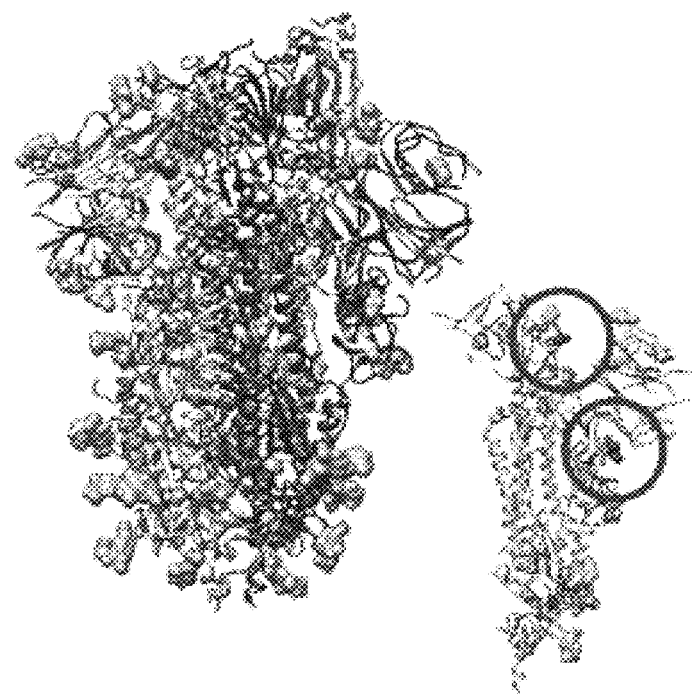

Embodiments of the invention further include a method for treating or preventing viral infection, including applying therapeutic effective amount of the compounds to the targeted subjects. The subject being treated can be human or animal. Preferably, the pharmaceutical composition is applied by the use of a spray or an inhalant.

Other embodiments, objects, and advantages of the invention will be apparent to those skilled in the art from the following detailed description taken in conjunction with the appended claims and drawings.

BRIEF DESCRIPTION OF THE FIGURES

FIG. 1A is a schematic depiction of the entry mechanism of SARS-CoV-2.

FIG. 1B depicts a structure of a Spike protein.

FIG. 1C depicts four most common glycans attached the Spike protein (■; N-acetylglucosamine, ●; mannose, ▲; fucose, ●; galactose, ♦; sialic acid).

FIG. 2A depicts a domain structure of mammalian PNGase with the PUB, TG and PAW domains.

FIG. 2B depicts a tridimensional structure of mouse PNGase core (PDB ID: 2F4O), showing the TG domain and the zinc-binding domain. The structure contains the covalently-attached caspase inhibitor Z-VAD-FMK (carboxybenzyloxy-Val-Ala-Asp-a-fluoromethyl ketone), in the location associated with peptide binding.

FIG. 2C depicts an oligosaccharide removal reaction catalyzed by PNGase.

FIG. 3 depicts a delivery of an example of the invention (CROWNase) to the lungs of COVID-19 patients by inhaler. CROWNase binds tightly to the glycosylated Spike protein, through the ACE2 receptor, blocking virus attachment.

FIG. 4A depicts a model of N-linked glycan with and without fucose in h-PNGase isoform 1.

FIG. 4B shows results from SDS-PAGE of Spike protein treated with PNGase.

FIG. 4C shows other results from SDS-PAGE of Spike protein treated with h-PNGase.

FIG. 4D shows results from an immunohistochemistry experiment of Vero E6 cells transformed with liposomes containing the Spike protein treated with PNGase.

FIG. 4E shows results from Western blot experiment of Vero E6 cells transformed with liposomes containing the Spike protein treated with PNGase.

FIG. 4F is another example of immunohistochemistry of Calu-3 cells transformed with liposomes containing the Spike protein and the GAPDH gene.

DETAILED DESCRIPTION OF THE INVENTION

Unless defined otherwise, all technical and scientific terms used herein have the same meaning as commonly understood by one of ordinary skill in the art to which this invention belongs. As used in the specification and appended claims, unless specified to the contrary, the following terms have the meaning indicated. With regard to this specification, any time a definition of a term as defined herein, differs from a definition given for that same term in an incorporated reference, the definition explicitly defined herein is the correct definition of the term.

The words "a" and "an" denote one or more, unless specifically noted.

"Polypeptide" and "protein" are used interchangeably herein and mean any peptide-linked chain of amino acids, regardless of length or post-translational modification.

Abbreviations used herein are of common usage in the art, e.g., "PNGase" refers to peptide N-glycosidase, "ACE2" refers to angiotensin-converting enzyme 2.

"Fusion protein" is a protein comprising amino acid sequences from at least two different sources. A fusion protein can comprise amino acid sequence that is derived from a naturally occurring protein or is substantially homologous to all or a portion of a naturally occurring protein, and in addition can comprise amino acids that are synthetic sequences. "Substantially similar" or "substantially homologous" refers to at least 50% sequence identity, desirably more that 50% sequence identity, such as each 1% increment over 50%, and desirably at least 60%, 70%, 80%, or 90%, and preferably greater than 90%, such as 91%, 92%, 93%, 94%, 95%, 96%, 97%, 98%, or 99% sequence identity.

Coronaviruses are enveloped positive single-stranded RNA viruses. Members of this family are among the largest RNA viruses known, with virions ranging from 118 to 136 nm in diameter and genome sizes from 25 to 32 kb (49). Virions are spherical and have a large glycoprotein protruding from the envelope, the Spike protein, giving the appearance of a crown under the microscope. The genome size of the SARS-CoV-2 virus is approximately 30 kb, encoding 15 non-structural proteins, 4 structural proteins, and 8 auxiliary proteins (50). The structural proteins are the Spike glycoprotein, small envelope glycoprotein E, membrane glycoprotein M, and the nucleocapsid protein. The three glycoproteins are embedded or tightly associated to the membrane. Glycoprotein M has roles in determining the shape of the virus envelope and stabilizing the nucleocapsid (51). Glycoprotein E is involved in production and maturation of the virus (52) and the N protein binds to the RNA genome, forming the nucleocapsid (51). The Spike glycoprotein is particularly important, as this is the viral component involved both in host cell recognition and cell infection, through the fusion of the viral envelope with the cell membrane (18).

Recent studies have shown that the Spike protein binds tightly to the angiotensin-converting enzyme 2 receptor (ACE2), found in the membrane of the host cell (53, 54), the same receptor used by the SARS-CoV-1 virus to infect cells. Remarkably, the binding of SARS-CoV-2 to this receptor is 10-20 times stronger, explaining the very high infectivity of COVID-19 virus (54, 55). The Spike protein is homotrimeric and highly glycosylated (56, 57). Each monomer has an ectodomain, comprising the majority of the protein, a single transmembrane helix and a short internal C-terminal tail (56). The ectodomain contains two smaller regions (also known as subunits), the receptor binding S1 subunit and the membrane-fusion S2 subunit. Upon attachment of the receptor binding domain in S2 to the ACE2 receptor, the spike protein is cleaved at the S1/S2 boundary region and at the S2' site by TMPRSS2 and other proteases found in the host membrane (56). The proteolytic cleavage of the spike protein triggers the formation of a six-helix bundle fusion core complex by the Heptad repeat 1 and 2 domains in the S2 subunit, which brings the virus and host membrane together and mediate membrane fusion, allowing the release of the genetic material into the host cell, completing the infection process (19, 56, 58) (FIG. 1A).

As indicated previously, the N-glycosylation of the Spike protein is a critical structural factor that allows the virus to escape the immune system. Moreover, several studies indicate the N-linked glycans play an essential role in cell entry and that their removal halts SARS-CoV-2 infection. For instance, site-directed mutagenesis of predicted N-glycosylation sites N212D, N276D and N283D of the spike protein of infectious bronchitis virus (IBV) coronavirus resulted in inhibition of a cell-cell fusion model of Vero cells (32). Remarkably, mutations of these three N-glycosylation sites completely stop IBV viral replication (32). Two of these sites, N282 and N343 (located in the N terminal domain and receptor binding domain respectively) are conserved in SARS-CoV1 and SARS-CoV-2 (FIG. 1B), indicating that they play similar roles.

Figures 1C, 2A:
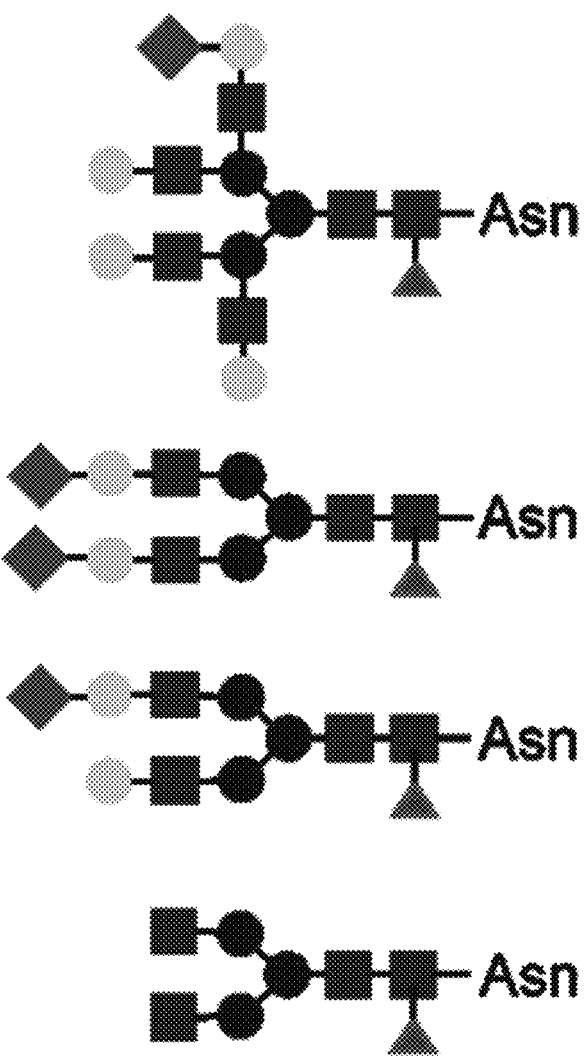
Figure 2B:
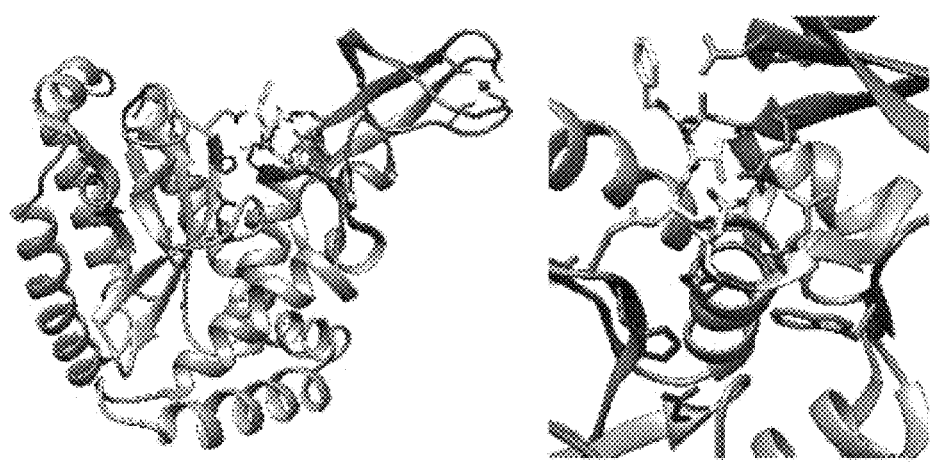
Figure 2C:
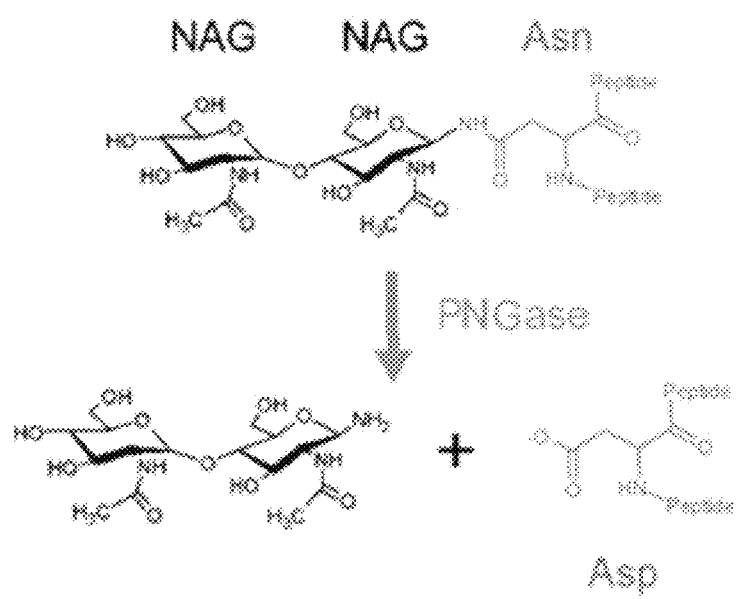

PNGase (peptide N-glycosidase) catalyzes the hydrolysis of the amino bond between the first N-acetylglucosamine residue of N- attached glycans and a conserved asparagine residue in the protein, producing aspartate and a free glycan with an amino group attached to the proximal N-acetyl glucosamine (NAG) (FIG. 2C). The amino group is spontaneously hydrolyzed, producing the free glycan with two β (1-4) NAG residues (i.e. N—N-diacetylchitobiose) in the reducing end (70). PNGase catalytic activity is highly variable and depending on the species, it can process high mannose, hybrid, or complex oligosaccharides (70-73), and native or denatured glycosylated peptides (74, 75). SARS-CoV, MERS-CoV, and SARS-CoV-2 spike protein glycans are for the most part complex, carrying NAG as the second sugar residue in the branches and an α (1-6) fucose residue in the proximal NAG residue (57, 59) (FIG. 1C). PNGase is a very important part of the protein homeostasis mechanisms in the cell, processing misfolded or nonfunctional glycosylated proteins. The non-functional proteins are retrotransported from the endoplasmic reticulum to the cytoplasm. In the cytoplasm, PNGase removes the glycans, allowing the degradation of the peptide by the proteasome and the oligosaccharide by diverse glycosidases (76, 77).

In contrast with bacteria, unicellular fungi, and plants, which contain the active core (Transglutaminase; TG) of the enzyme as the only domain, the human enzyme contains two additional domains: the PUB (PNGase and UBiquitin related) and the PAW (PNGase And other Worm proteins) domains (70). FIG. 2B shows the structure of the mammalian TG core domain, composed of a central highly curved β-sheet with six antiparallel strands, stabilized by eight a-helices. The TG core domain binds the β (1-6) NAG dimer (N—N-diacetylchitobiose) (78) and the peptide region carrying the glycosylated asparagine (79), and also carries the catalytic triad of conserved cysteine, histidine, and aspartate residues involved in the de-glycosylation reaction (80, 81). The TG domain also includes a three-stranded beta-sheet zinc binding domain, which forms the "lid" of the peptide binding site (79, 82). The PAW domain is also able to bind oligosaccharides, in particular high-mannose glycans with three branches (70, 83). The PUB domain appears to be regulatory and binds to several proteins involved in the proteasome function (79, 84, 85).

The invention provides compositions and methods of using the TG catalytic core and PAW domains to remove SARS-CoV-2 glycan shield. Embodiments of the invention include a fusion protein (referred to herein as "CROWNase") that can remove the glycan shield of SARS-CoV-2 virus, stopping the entry of the virus into the cell and exposing the antigenic components of the virus to the immune system, allowing the quick development of an appropriate immune response by the body.

Figures 3, 4A:
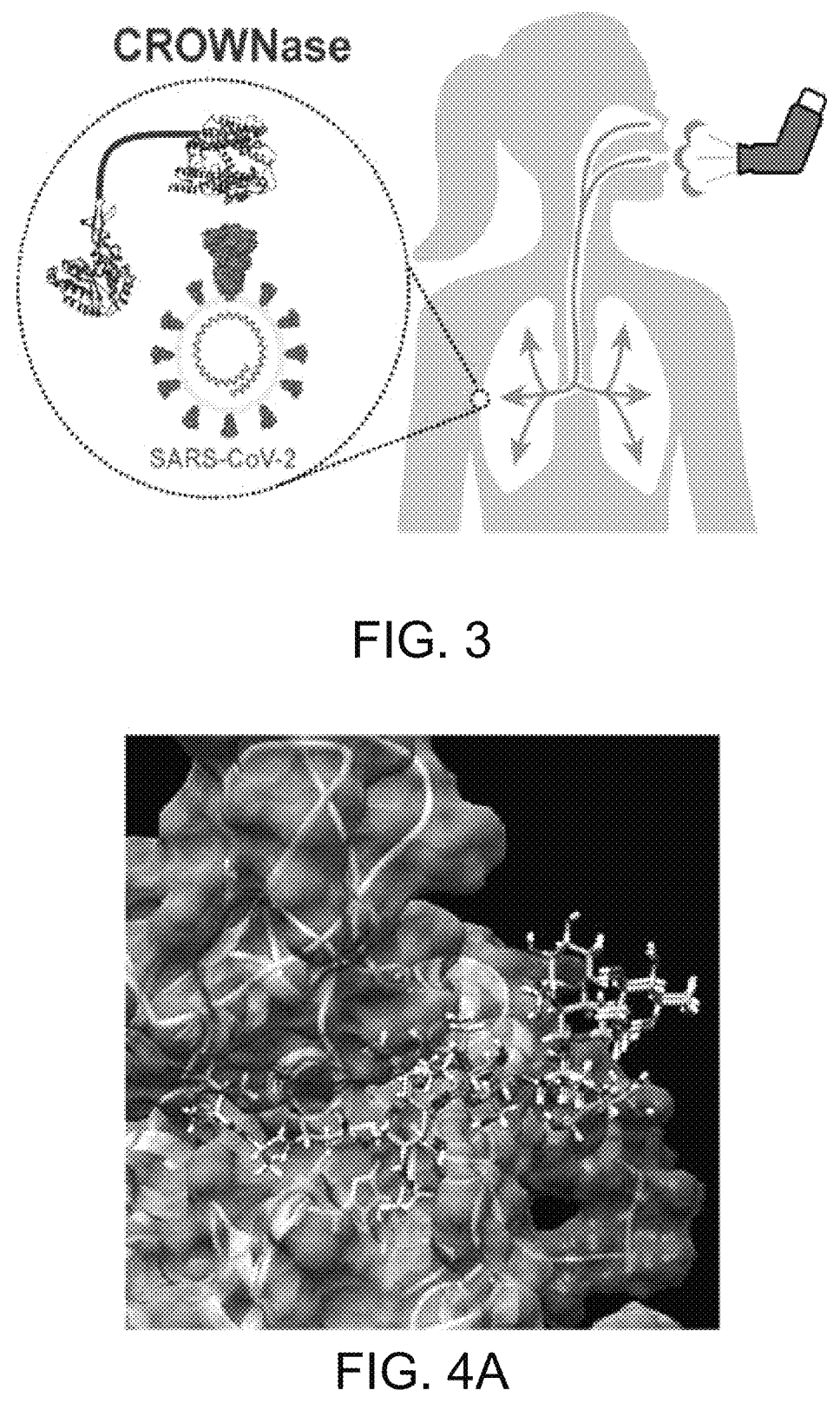

Embodiments of this invention include CROWNase, including domains of h-PNGase and improves the performance of h-PNGase. Mutation sites found in highly active homologous enzymes that stabilize high-energy conformations of the substrate and lead to an improved catalytic rate are introduced to catalytic site. The PAW domain of h-PNGase, which is involved in substrate affinity and specificity, is modified to improve the affinity for the types of glycans found in the Spike protein. The PAW domain can be also substituted for an affinity-enhancing domain which include another protein (e.g. galectin) that can bind more tightly to the complex. CROWNase further adds the ACE2 receptor to the engineered h-PNGase. FIG. 3 demonstrates the example of delivery of CROWNase to the lungs of COVID-19 patients. CROWNase binds tightly to the glycosylated Spike protein, through the ACE2 receptor, blocking virus attachment. This enzyme removes the virus glycan layer through the activity of engineered h-PNGase. CROWNase further includes a connecting domain that comprises a highly flexible loop of about 10 amino acid residues to connect both h-PNGase domain and ACE2 receptor, to allow h-PNGase to reach to the virus and carry out its function. Examples of a connecting domain can include polyglycine or sequences from the protein itself, e.g., the sequence between the TG and PAW domains. To stabilize the construct for improved delivery through an inhaler, solvent-accessible and hydrophobic regions of the protein can be replaced with hydrophilic residues.

Embodiments of the invention include a protein compound that has PNGase activity, catalyzing the cleavage of a beta-aspartyl-glucosamine and the amide side chain of Asn, converting Asn to Asp and free glycan. Such embodiments can also include a protein compound that has endo-beta-N-acetylglucosaminidase (ENGase) activity, cleaving the beta-1,4-glycosidic bond of an N,N'-diacetylchitobiose core. Other examples of embodiments include compounds removing the alpha glycosidic bond between the proximal NAG and fucose (e.g., fucosidase), compounds removing the alpha glycosidic bond between sialic acid and the terminal antennary galactose residue (e.g. Sialidase or neuraminidase, compounds removing the alpha bonds between galactose molecules at the base of the antenna and the beta bond between the second NAG and the galactose molecule (e.g., alpha and beta-manosidases), compounds removing the beta glycosidic bond between the antennary mannose and NAG residues (e.g., hexosaminidase), and compounds removing the beta bond between the NAG and galactose molecule in the antenna (e.g., beta-galatosidase).

Embodiments of the invention include compounds formulated as pharmaceutical compositions, which include a therapeutically effective amount of the compound. Depending on the target cell, the compounds of the invention can be formulated as tablets, capsules for oral administration, solutions, suspensions, inhalants or nasal sprays. The therapeutically effective amount of the compound depends on the route of administration, condition and physical characteristics of the patients, and are tailored to achieve a desired therapeutic effect. The compounds can be designed for human use or animal use. The invention further includes the method of treating and preventing infection by viruses such as SARS-CoV-2 by applying the therapeutically effective amount of the compounds. In the case of SARS-CoV-2 virus, as it primarily infects the upper respiratory tract of the patient, the preferred embodiment is applying the compound in the form of nasal spray or inhalants. Embodiments of the invention can be also administered orally or delivered topically to the eyes in the forms of drops, sprays or ointments to prevent and treat the infection.

The invention also includes methods of inactivating viruses by glycosidases, which remove the glycan (sugar) coating from the surface proteins. Examples of such glycosidases include PNGase, endo-beta-N-acetylglucosaminidase (ENGase), fucosidase, mannosidase sialidaseglatactosidase, neuramidiase, hexosaminidase, aspartylglucosaminidase and their combinations. Examples of viruses include SARS-CoV-2, other known coronaviruses, and enveloped viruses in general, which depend on N-glycosylation for attachment and infection.

The present invention is described in further detail in connection with the following examples which illustrate or simulate various aspects involved in the practice of the invention. It is to be understood that all changes that come within the spirit of the invention are desired to be protected and thus the invention is not to be construed as limited by these examples.

EXAMPLES

De-Glycosylation of SARS-CoV-2 Spike Protein by PNGase

Figure 4B:
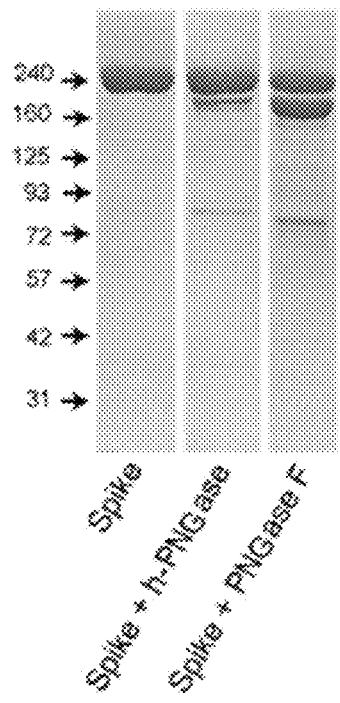

A tridimensional model of the TG core domain of isoform 1 of h-PNGase was built using the I-TASSER server (88-90), mostly based on crystal structures of mouse PNGase. A Val-Ala-Asn peptide was placed into the model based on the crystallographic position of the inhibitor Z-VAV-FMK. An oligosaccharide carrying an a fucose residue in the proximal NAG residue, similar to the complex-type glycans found in the spike protein, was N-linked to the peptide using the glycoprotein builder on the GLYCAM server (91) (FIG. 1C). As shown in FIG. 4A, the predicted site of h-PNGase isoform 1 can accommodate the glycan in a pose that would allow the catalytic triad to perform the de-glycosylation. To corroborate that PNGase is able to remove the complex oligosaccharides in the native Spike protein, the 6×-His tagged h-PNGase isoform 1 was cloned and purified with a purity of 80%. Tests with commercially available PNGase F from the bacterium *Elizabethkingia meningoseptica* (New England Biolabs) were carried out. The native glycosylated Spike protein, containing the S1, S2, transmembrane, and internal domains was purchased from Fisher Scientific (catalog number: 50-196-3983) and was passed once through gel filtration chromatography to eliminate impurities. PNGase F or h-PNGase (0.1 mg/ml) were incubated for 1 h at 37° C. with the spike protein trimer (2 mg/ml) in Gamble's saline medium (pH 7.4), which resembles the composition of the extracellular liquid found in the lungs (92). The reaction was stopped with the addition of 0.1% SDS and the samples were run under denaturing conditions in SD S-PAGE. The molecular weight of the fully glycosylated spike protein monomer is 220-250 kDa and upon removal of all glycans its molecular weight decreases to the predicted size of the polypeptide, 170 kDa (93). The commercially available Spike protein appears to be a population of species with different molecular weights, with a relatively diffused band spanning 200-260 kDa (FIG. 4B). The incubation with PNGase F produces two diffuse bands of 230 and 180 kDa, indicating that the enzyme is able to remove the glycan shield. The incubation with human PNGase isoform 1 also produces species of lower molecular weights but with a different pattern, with minor bands of 200 and 180 kDa and with a seemingly lower activity. The lower activity could be due in part to the presence of the 6×-His Tag. These results indicate that both the human and commercially available PNGase are able to remove the glycan shield of the native Spike protein.

Inactivation of Spike Protein-Mediated Membrane Fusion by PNGase

Figure 4C:
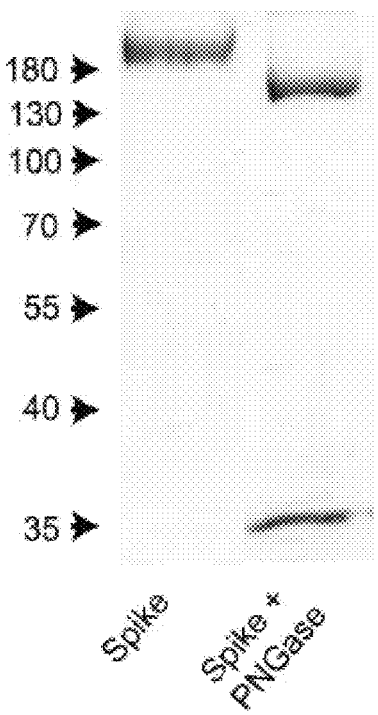

To test that the de-glycosylation of the spike protein by PNGase inactivates virus entry, a virus-free assay is developed with the spike protein incorporated into artificial proteoliposomes. As reported extensively in the literature, the Spike protein solely carries out binding to the receptor and entry into the cell (56). In this method, the commercially-available full-length Spike protein was resuspended in Gamble's buffer containing 0.3% b-D-dodecylmaltoside, a gentle non-detergent that preserves the structure of membrane proteins. The solubilized spike protein was mixed with membrane lipid extract from liver (Avanti Polar Lipids) with 0.5 M octyl-glucoside. The slow removal of detergents by Riorad BioBeads allows the formation of tightly sealed artificial proteoliposomes. This technique was extensively used to reconstitute large bacterial membrane complexes into impermeable and stable liposomes (94-96). In this case, the solution with the lipids and the Spike protein contained Myc-tagged human GADPH gene into the pCMV-Myc plasmid, which is incorporated into the liposomes serving as a reporter of the ability of the liposomes to be fused with mammalian cells. The proteoliposomes were incubated with Vero cells, which carry the ACE2 receptor and TMPRSS2 protease and can be infected by SARS-CoV-2 (97, 98). The cells were fixed and an anti-Myc antibody was used to visualize transformed cells by immunohistochemistry. FIG. 4C shows another example of inactivation of the Spike protein by CROWNase, with SDS-PAGE of Spike protein treated with h-PNGase.

Figure 4D:
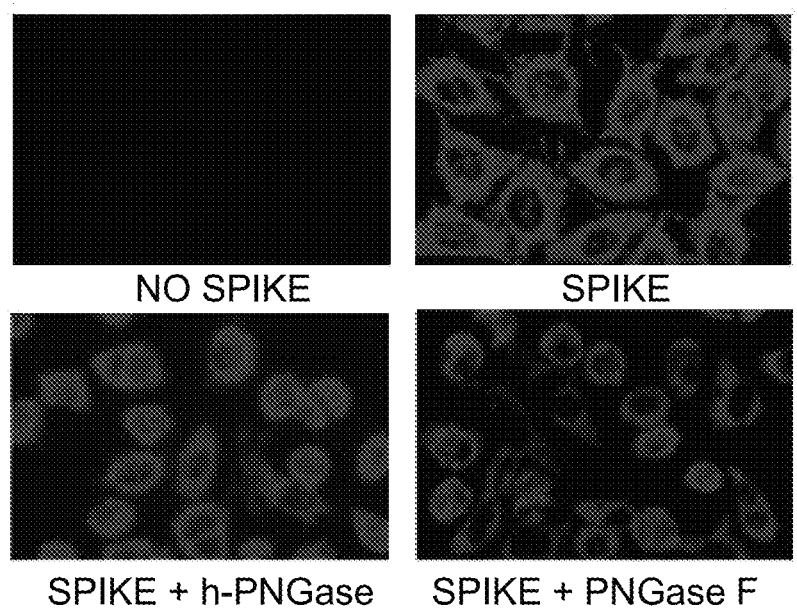
Figure 4E:
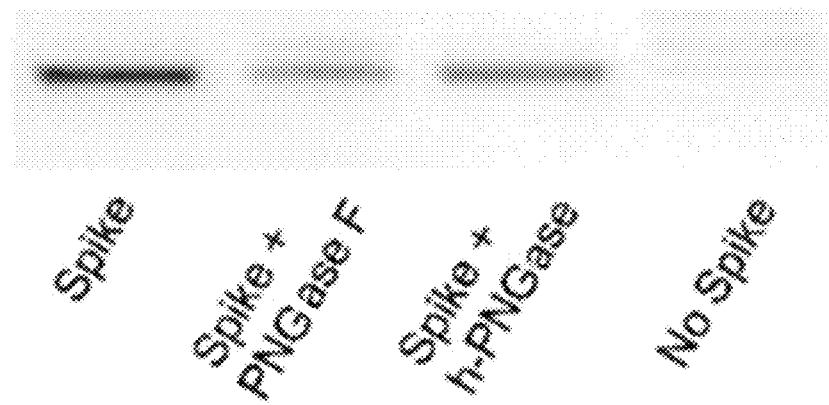
Figure 4F:
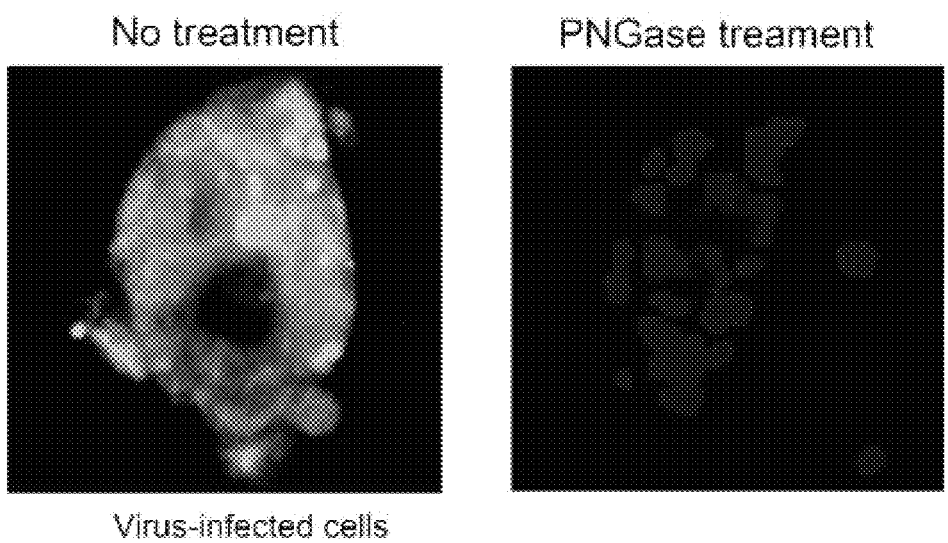

As shown in FIG. 4D, proteoliposomes with the reconstituted Spike protein were able to effectively deliver the GAPDH gene to the cells and those without the spike protein delivered the recombinant gene with a low efficiency, as expected. Remarkably, proteoliposomes carrying the spike protein that were incubated with the human and bacterial PNGases for 2 hours showed a significant decrease (30% and 60%, respectively) in the ability to deliver the GAPDH gene. These effects were confirmed by western blot against the Myc-tag (FIG. 4E). The results demonstrate that h-PNGase is able to inactivate the spike protein-mediated fusion by removing the glycan coating. FIG. 4F is another example of immunohistochemistry of Calu-3 cells transformed with liposomes containing the Spike protein and the GAPDH gene after a 20 min treatment with PNGase treatment. DNA was stained with Hoescht, GAPDH stained with anti-myc (grey).

Identification of h-PNGase Isoforms that Inactivate SARS-CoV-2

1. Human PNGase Purification

It has been reported that PNGase is ubiquitous in the body, with an activity that varies enormously (by up to 2 orders of magnitude) in different organs, with the highest activity found in the liver and testes (99), suggesting that the isoforms could have very different kinetic properties and selectivity. The human genome contains a single gene coding for PNGase (NGLY1). This gene produces 8 isoforms (isoforms 1-4 and X1-X4) due to alternative splicing (100). cDNA for isoforms 1-4 is acquired (Genecopoeia) and specific primers for each of the isoforms are used to produce the PCR amplicons, which can be cloned into the pBAD-HisB expression vector with a 6xHis tag, to allow a quick one-step purification of the enzymes. The predicted h-PNGase isoforms X1-X4 can be synthesized (biomatik) and similarly cloned into pBAD/HisB. The 6xHis tag is located in the C-terminus, separated from the h-PNGase by a flexible 4xGly linker and by the TEV protease sequence (ENLYFQS), to eliminate the 6xHis tag (101), which has shown to decrease the activity of several proteins (102).

2. Spike Protein Purification

The full-length SARS-CoV-2 spike DNA sequence, with a C-terminal 4xGly linker and a 6xHis tag, can be synthesized from cDNA prepared from genomic RNA (ATCC) and cloned into the mammalian expression vector pαH, such as using methods described in the literature (31, 54). The FreeStyle 293-F cells are transfected with the pαH-S construct (54). These cells have high transfection efficiencies and can reaching high density in suspension, which allows the production of large amounts of recombinant protein. Previous reports indicate that the Spike proteins obtained from these cells carry their native fold and contain the expected glycosylation pattern (31, 54).

3. Activity Measurements

The activity of the isoforms can be tested using the Spike protein produced as described above. PNGase activity can be measured by Western blot, following the molecular weight of the spike protein, using rabbit polyclonal antibody against the SARS-CoV spike protein (SARS-Sm antibody, Abgent). However, this method has a limited resolution, is time-consuming, and it is only semiquantitative. To obtain steady-state kinetic rates, the recently developed 96-well plate colorimetric technique by Wang, T et al. (103) can be used, based on the reaction of the tetrazolium dye WST-1 (2-(4-Iodophenyl)-3-(4-nitrophenyl)-5-(2,4-disulfophenyl)-2H-tetrazolium) with the reducing end of the polysaccharide produced by PNGase. Steady state activity rates are measured at different concentrations of the spike protein substrate, allowing the calculation of the kinetic parameters Vmax and Km for the eight isoforms of h-PNGase. The isoform that shows the highest Vmax and lowest Km (indicating high activity and affinity) can be selected for further tests, in particular for protein engineering experiments.

4. PNGase Crystallization

The h-PNGase isoform (or isoforms) that show the highest activities or affinities can be crystalized. There are currently only two eukaryotic PNGases crystallized, from yeast (PDB: 3ESW) and mouse (2F4O). The main objectives of the crystallization experiments are to obtain the tridimensional structure at high resolution (ideally <2.0 Å) of the whole protein and to solve the complex with the substrates (i.e., asparagyl-chitobiose) or substrate analogs, to reveal atomic-level interactions between the substrates and the protein. As a starting point, conditions previously reported for the mouse PNGase crystallization (82) are used. In addition, new conditions for protein crystallization can be screened, which could be obligatory for protein-substrate complexes. The protein-substrate complexes can be explored by direct co-crystallization and by protein-crystal soaking with various concentrations of the substrates. Initial screening for crystal growth can be performed for 100-400 nL protein-solution droplets by sitting-droplet vapor-diffusion method, using Mosquito crystallization robots and 96-well CystalQuick Greiner plates. If necessary, larger crystallization droplets can be set up manually. Once high-quality crystals are obtained, protein structures can be determined based on the previously used procedures (104). Diffraction data can be collected at 100 K at the 19-ID (105) and 19-BM beamlines of the Structural Biology Center at the ANL Advanced Photon Source (APS). The structures can be determined by molecular replacement (MR) method using available structures from Protein Data Bank (PDB) and the HKL3000 program suite (106) incorporating MOL-REP (107), SOLVE/RESOLVE (108) and ARP/wARP (109) programs. Initial models can be completed by manual modeling using COOT program (110) and refined using the REFMAC program (111) from CCP4 suite (112). The stereochemistry of the structures can be validated with PHENIX suite (113) incorporating MOLPROBITY tools (114).

5. Spike Protein-Mediated Liposome Fusion

These experiments can be carried out to test the effects of different PNGase isoforms on the ability of Spike protein-containing proteoliposomes to deliver GAPDH to Vero E6 cells.

6. In Vitro SARS-CoV-2 Infectivity Test

To demonstrate that the de-glycosylation by PNGase inactivates the virus and prevents the infection by stopping membrane fusion, the effects of the incubation of h-PNGase with the SARS-CoV-2 virus can be tested. Calu-3 (lung carcinoma cell line) and Vero E6 cells are ideal to perform SARS-CoV-2 infection assays since they express the ACE2 receptor and produce high virus titers (97, 115). Polarized monolayers of Calu-3 and Vero E6 cells can be grown in Dulbecco minimal essential media (DMEM), supplemented with heat-inactivated fetal bovine serum (10%) and antibiotic/antimycotic mixture. Infection of Vero E6 and Calu-3 cells can be evaluated as the formation of plaques 48 hours post-infection (hpi) (115). The virus inoculum can be incubated for different times and with different concentrations of h-PNGase. Cells can be incubated at 37° C. for 2 hr and the unbound viral inoculum is washed with PBS. Cultures can be overlaid with culture media plus 0.8% agarose and after 48 hpi plaques be visually quantified by neutral red staining (116). Additionally, Western-blotting can be performed from total protein extracted from the infected cultures to detect the presence of the viral proteins using a rabbit polyclonal serum against the SARS-CoV-2 spike protein (40150-T52, Sino Biological).

7. Alternative Strategy

A construct taking the TG core domain of the isoform with the highest activity and the PAW domain of the isoform with the lowest Km can be made. The TG core carries the residues involved in catalysis (81) and thus it determines the Vmax, and the PAW domain determines the affinity and specificity (78, 83) of the enzyme and thus Km. Moreover, to identify if some of the isoforms have an intrinsic low activity, they can be tested using RNase, a preferred substrate of most PNGases (103). The tests can be conducted with the folded and heat-denatured RNase, since some PNGases act specifically on denatured samples (74). It is likely that some of the h-PNGase isoforms would not be highly active due to the steric hindrance of sugars interfering with the ability of the enzyme to find the binding site. If the de-glycosylation process is too slow, the effects of other human enzymes normally involved in oligosaccharide degradation can be tested. For instance, other commercially available human enzymes (New England Biolabs): 1) α-mannosidase Man2Cl, which removes the mannose branches from glycans in the cytosol (117, 118), 2) (β-Hexosaminidase A, which removes the distal NAG from oligosaccharide branches (119), and 3) Fucosidase, which removes the a (1-6) fucose reside in the proximal NAG (120). highly active isoforms that require no other glycosidase can be prioritized, but if these enzymes produce a significant effect (i.e., decrease of more than one order in magnitude in the inactivation time or PNGase concentration), they can be incorporated into the CROWNase chimera. It is also possible that some of the PNGase isoforms would not be stable during the purification. In this case, they can be co-expressed with the proteasome p97 protein, which has allowed the purification of mouse PNGase (83).

Protein Engineering and CROWNase Design

1. Chimera Construction

The CROWNase chimera desirably binds tightly to the SARS-CoV-2 virus. This can be achieved by including the soluble domain of the ACE2 receptor in the construct. It has been shown that the Spike protein has a very high affinity for the ACE2 receptor (nM range) (121). Moreover, studies with RBD fragments demonstrate that the glycosylation state of RBD does not modify its binding with ACE2 (122, 123), and thus de-glycosylation of the Spike protein by PNGase would not release CROWNase from the virus.

The human ACE2 fragment encoding for the soluble portion, residues 19-615 (124), can be amplified by PCR from a cDNA clone (NM_021804.2, GeneCopoeia) and cloned into a pBAD/HisB expression vector with a C-terminus 6x-His tag for purification. BL21 E. coli cells can be transformed with the constructs for protein expression. To verify that the purified ACE2 soluble domain retains its native fold and function, binding analysis with the Spike protein can be carried out by isothermal titration calorimetry. The chimera can be constructed by cloning both genes together in frame. A highly flexible loop of 5-20 amino acid residues connecting both domains can be introduced, to allow h-PNGase to reach to the virus and carry out its function. The activity of the chimera can be tested for its ability to de-glycosylate the Spike protein and to prevent liposome fusing. Depending on the kinetic parameters obtained the sequence of the linking peptide can be modified, to make it longer, more rigid or to modify its polarity. Chimeric proteins with high de-glycosylation activities can be tested against the SARS-CoV-2 virus in vitro, using the methods described above.

2. h-PNGase Enzyme Engineering: Activity Enhancement h-PNGase can be engineered to enhance the rate at which it can process complex glycans. The TG and PAW domains are designed to increase the activity and affinity of the enzyme, depending on the kinetic data obtained. If turnover is limited by the catalytic step, the core domain can be prioritized for engineering. If it is limited by substrate binding, then the PAW domain can be prioritized. Mutations in the core domain can be inspired by variations observed in other species, in particular by the PNGases from *Aspergillus tubingensis* and the commercially available PNGase F from *E. meningoseptica*, which are the most active enzymes (73, 125). Quantum mechanics/molecular mechanics (QM/MM) calculations (126) can be used to evaluate the extent to which variations of the core domain stabilize the tetrahedral transition state where the catalytic cysteine is covalently bonded to both the scissile carbonyl and the amine of the glycan. Variations that most substantially reduce the energetic barrier to transition are expected to provide the largest increases in activity.

Studies with mammalian PNGase show that the PAW domain determines the specificity and overall affinity of the protein (83). The PAW domain of the mouse enzyme binds 5 mannose residues at the branching point of the oligosaccharide. The crystal structure reveals that three of the mannose residues are bound tightly to this site through extensive H-bonding interactions. Interestingly, the most proximal and most distal mannoses are relatively loose (83), which might explain the low affinity observed in the enzymes from different organisms (81, 103, 125, 127). This domain does not appear optimal to bind the complex glycans observed on the SARS-CoV-2 spike. Mutations to residues in contact with the glycan, in particular those in the distal positions, can be prioritized for expression and biochemical assays based on molecular modeling (as a starting point) and on the tridimensional structure of the TG and PAW domains, when they are available. Mutants in which binding free energy calculations predict to have a reasonable affinity for the complex glycan can be prioritized for testing. Introducing residues in these positions that can form hydrogen bonds with the sugar likely can increase the affinity of the site.

3. h-PNGase Enzyme Engineering: Stability Enhancement

Major concerns with delivering protein therapeutics by inhalation are unfolding and aggregation due to nebulization stresses. These concerns are addressed by engineering the protein to increase its stability by making it more soluble. Common strategies to increase protein solubility include replacing hydrophobic surface residues with hydrophilic ones and shifting the pI away from the physiologic pH (128). Crystallographic studies have identified L431, I435, L438, V439, and L442 of mouse PNGase (highly homologous to human) as a hydrophobic face of helix 12 that enables its interaction with the regulatory protein HR23 (82). Similarly, I54 is part of a hydrophobic pocket that mediates the interaction between PNGase and p97, a protein proposed to facilitate endoplasmic reticulum-associated protein degradation (129). As these protein-protein interactions of cytosolic PNGase are unnecessary for therapeutic purposes herein, these regions can be targeted for site-directed mutagenesis. Additional regions can be identified based on computer simulations of the enzyme's atomistic molecular dynamics. Molecular dynamics simulations can be analyzed to obtain the surface aggregation propensity (130) and identify hydrophobic patches on the enzyme. Molecular modelling can be used to prioritize mutants predicted to most significantly improve solubility. Initially, modelling can be based on the fast and computational inexpensive generalized Born implicit solvent model (131). As data on the stability of mutants can be accumulated, they can be used to refine computational predictions. If the generalized Born solvation model is unsuccessful at reproducing experimental stability trends, alternative strategies include: the domain decomposition Conductor-like Screening model (132), the quantum mechanical approach that accounts for polarization, or the free energy calculations for the ensemble of accessible protein conformations (133), or machine learning methods.

4. ACE2 Protein Engineering: Stability Enhancement

The stability of the PNGase-ACE chimera can be enhanced with guidance from the molecular modeling techniques to engineer PNGase. Regions that can be prioritized for substituting hydrophobic with hydrophilic residues include the interdomain areas and the linker between PNGase and ACE2.

Thus, the invention provides compositions and methods for treating viral infections. The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

REFERENCES

1. Zhou et al. (2020) A pneumonia outbreak associated with a new coronavirus of probable bat origin. *Nature.* 579, 270-273
2. Fehr, A. R., and Perlman, S. (2015) Coronaviruses: An Overview of Their Replication and Pathogenesis. *Coronaviruses.* 1282, 1-23
3. Donnelly et al., Worldwide Reduction in MERS Cases and Deaths since 2016—Volume 25, Number 9—September 2019—Emerging Infectious Diseases journal—CDC. 10.3201/eid2509.190143
4. Chowell et al., (2004) Model Parameters and Outbreak Control for SARS. *Emerg Infect Dis.* 10, 1258-1263
5. Park, J.-E., Jung, S., Kim, A., and Park, J.-E. (2018) MERS transmission and risk factors: a systematic review. *BMC Public Health.* 10.1186/s12889-018-5484-8
6. El-Aziz, T. M. A., and Stockand, J. D. (2020) Recent progress and challenges in drug development against COVID-19 coronavirus (SARS-CoV-2)—an update on the status. *Infect Genet Evol.* 10.1016/j.meegid.2020.104327
7. Coronavirus [online] https://www.who.int/emergencies/diseases/novel-coronavirus-2019 (Accessed May 24, 2020)
8. The Global Economic Impacts of COVID-19 [online] https://www.csis.org/analysis/global-economic-impacts-covid-19 (Accessed May 24, 2020)
9. Sambhara, S., and McElhaney, J. E. (2009) Immunosenescence and Influenza Vaccine Efficacy. in *Vaccines for Pandemic Influenza* (Compans, R. W., and Orenstein, W. A. eds), pp. 413-429, Current Topics in Microbiology and Immunology, Springer, Berlin, Heidelberg, 10.1007/978-3-540-92165-3_20
10. Bolles et al., (2011) A Double-Inactivated Severe Acute Respiratory Syndrome Coronavirus Vaccine Provides Incomplete Protection in Mice and Induces Increased Eosinophilic Proinflammatory Pulmonary Response upon Challenge. *Journal of Virology.* 85, 12201-12215
11. Tseng et al., (2012) Immunization with SARS coronavirus vaccines leads to pulmonary immunopathology on challenge with the SARS virus. *PLoS ONE.* 7, e35421
12. Wang et al., (2016) Immunodominant SARS Coronavirus Epitopes in Humans Elicited both Enhancing and Neutralizing Effects on Infection in Non-human Primates. *ACS Infectious Diseases.* 10.1021/acsinfecdis.6b00006
13. Wang et al., (2020) Remdesivir and chloroquine effectively inhibit the recently emerged novel coronavirus (2019-nCoV) in vitro. *Cell Res.* 30, 269-271
14. CHEN Jun, L. D., and CHEN Jun, L. D. (2020) A pilot study of hydroxychloroquine in treatment of patients with moderate COVID-19. *J Zhejiang Univ (Med Sci).* 49, 215-219
15. Commissioner, O. of the (2020) Coronavirus (COVID-19) Update: FDA Issues Emergency Use Authorization for Potential COVID-19 Treatment. *FDA.* [online] https://www.fda.gov/news-events/press-announcements/coronavirus-covid-19-update-fda-issues-emergency-use-authorization-potential-covid-19-treatment (Accessed May 27, 2020)
16. NIH clinical trial shows Remdesivir accelerates recovery from advanced COVID-19 (2020) *National Institutes of Health (NIH).* [online] https ://www.nih.gov/news-events/news-releases/nih-clinical-trial-shows-remdesivir-accelerates-recovery-advanced-covid-19 (Accessed May 27, 2020)
17. Liu et al., (2020) Research and Development on Therapeutic Agents and Vaccines for COVID-19 and Related Human Coronavirus Diseases. *ACS Cent. Sci.* 6, 315-331
18. Li, F. (2016) Structure, Function, and Evolution of Coronavirus Spike Proteins. *Annu Rev Virol.* 3, 237-261
19. Walls, et al., (2020) Structure, Function, and Antigenicity of the SARS-CoV-2 Spike Glycoprotein. *Cell.* 181, 281-292.e6
20. Ou, et al., (2020) Characterization of spike glycoprotein of SARS-CoV-2 on virus entry and its immune cross-reactivity with SARS-CoV. *Nature Communications.* 11, 1620
21. Shang, J., Wan, Y., Luo, C., Ye, G., Geng, Q., Auerbach, A., and Li, F. (2020) Cell entry mechanisms of SARS-CoV-2. *PNAS.* 10.1073/pnas.2003138117
22. Graham, R. L., and Baric, R. S. (2010) Recombination, Reservoirs, and the Modular Spike: Mechanisms of Coronavirus Cross-Species Transmission. *J Virol.* 84, 3134-3146
23. Li, F. (2013) Receptor recognition and cross-species infections of SARS coronavirus. *Antiviral Res.* 100, 246-254
24. Wu, K., Peng, G., Wilken, M., Geraghty, R. J., and Li, F. (2012) Mechanisms of Host Receptor Adaptation by Severe Acute Respiratory Syndrome Coronavirus. *J Biol Chem.* 287, 8904-8911
25. Cui, J., Li, F., and Shi, Z.-L. (2019) Origin and evolution of pathogenic coronaviruses. *Nat Rev Microbiol.* 17,181-192
26. Lewnard, J. A., and Cobey, S. (2018) Immune History and Influenza Vaccine Effectiveness. *Vaccines (Basel).* 10.3390/vaccines6020028
27. Forster, P., Forster, L., Renfrew, C., and Forster, M. (2020) Phylogenetic network analysis of SARS-CoV-2 genomes. *Proc. Natl. Acad. Sci. U.S.A.* 117, 9241-9243
28. ProductDevelopment, I. of M. (US) C. on A. R. D. R. and O., Field, M. J., and Boat, T. F. (2010) *Development of New Therapeutic Drugs and Biologics for Rare Diseases*, National Academies Press (US), [online] https://www.ncbi.nlm.nih.gov/books/NBK56179/ (Accessed May 24, 2020)
29. Clercq, E. D., and Li, G. (2016) Approved Antiviral Drugs over the Past 50 Years. *Clinical Microbiology Reviews.* 29, 695-747
30. Zhao, et al., (2015) Inhibition of endoplasmic reticulum-resident glucosidases impairs severe acute respiratory syndrome coronavirus and human coronavirus NL63 spike protein-mediated entry by altering the glycan processing of angiotensin I-converting enzyme 2. *Antimicrob. Agents Chemother.* 59, 206-216
31. Watanabe, Y., Allen, J. D., Wrapp, D., McLellan, J. S., and Crispin, M. (2020) Site-specific glycan analysis of the SARS-CoV-2 spike. *Science.* 10.1126/science.abb9983
32. Zheng, et al., (2018) Identification of N-linked glycosylation sites in the spike protein and their functional impact on the replication and infectivity of coronavirus infectious bronchitis virus in cell culture. *Virology.* 513, 65-74
33. van der Meer, et al., (2007) The carbohydrate-binding plant lectins and the non-peptidic antibiotic pradimicin A target the glycans of the coronavirus envelope glycoproteins. *J Antimicrob Chemother.* 60, 741-749

34. Ritchie, et al., (2010) Identification of N-linked carbohydrates from severe acute respiratory syndrome (SARS) spike glycoprotein. *Virology.* 399, 257-269
35. THL (1992) RECOMBINANT DNase THERAPY FOR CYSTIC FIBROSIS. *NEJM Journal Watch.* 10.1056/JW199204170000006
36. Thomson, A. H. (1995) Human recombinant DNase in cystic fibrosis. *JR Soc Med.* 88, 24-29
37. Bodier-Montagutelli et al., (2018) Designing inhaled protein therapeutics for topical lung delivery: what are the next steps? *Expert Opin Drug Deliv.* 15, 729-736
38. Ansun Biopharma, Inc. (2020) *DAS181 for COVID-19: A Phase II/III, Multicenter, Randomized, Placebo-Controlled, Double-Blind Study,* clinicaltrials.gov, [online] https://clinicaltrials.gov/ct2/show/NCT04354389 (Accessed May 17, 2020)
39. Inc, A. B. (2020) Ansun Biopharma Announces Positive Results from Investigator-Initiated Trial of Novel COVID-19 Treatment. [online] https://www.prnewswire.com/news-releases/ansun-biopharma-announces-positive-results-from-investigator-initiated-trial-of-novel-covid-19-treatment-301033871.html (Accessed May 15, 2020)
40. Dorscheid, D. R., Wojcik, K. R., Yule, K., and White, S. R. (2001) Role of cell surface glycosylation in mediating repair of human airway epithelial cell monolayers. *Am. J. Physiol. Lung Cell Mol. Physiol.* 281, L982-992
41. Guan, Y et al., (2003) Isolation and Characterization of Viruses Related to the SARS Coronavirus from Animals in Southern China. *Science.* 302, 276-278
42. Song, et al., (2005) Cross-host evolution of severe acute respiratory syndrome coronavirus in palm civet and human. *PNAS.* 102, 2430-2435
43. Low, D. E. (2004) *SARS: LESSONS FROM TORONTO,* National Academies Press (US), [online] https://www.ncbi.nlm.nih.gov/books/NBK92467/ (Accessed May 19, 2020)
44. Centers for Disease Control and Prevention (CDC) (2003) Severe acute respiratory syndrome—Singapore, 2003. *MMWR Morb. Mortal. Wkly. Rep.* 52, 405-411
45. Alsolamy, S., and Arabi, Y. M. (2015) Infection with Middle East respiratory syndrome coronavirus. *Can J Respir Ther.* 51, 102
46. Sikkema, et al., (2019) Global status of Middle East respiratory syndrome coronavirus in dromedary camels: a systematic review. *Epidemiol Infect.* 10.1017/S095026881800345X
47. Fan, Y., Zhao, K., Shi, Z.-L., and Zhou, P. (2019) Bat Coronaviruses in China. *Viruses.* 11, 210
48. Rabi, F. A., Al Zoubi, M. S., Kasasbeh, G. A., Salameh, D. M., and Al-Nasser, A. D. (2020) SARS-CoV-2 and Coronavirus Disease 2019: What We Know So Far. *Pathogens.* 10.3390/pathogens9030231
49. Payne, S. (2017) Family Coronaviridae. *Viruses.* 10.1016/B978-0-12-803109-4.00017-9
50. Wu, F et al., (2020) A new coronavirus associated with human respiratory disease in China. *Nature.* 579, 265-269
51. Astuti, I., and Ysrafil (2020) Severe Acute Respiratory Syndrome Coronavirus 2 (SARS-CoV-2): An overview of viral structure and host response. *Diabetes Metab Syndr.* 10.1016/j.dsx.2020.04.020
52. Schoeman, D., and Fielding, B. C. (2019) Coronavirus envelope protein: current knowledge. *Virology Journal.* 16, 69
53. Li, et al., (2003) Angiotensin-converting enzyme 2 is a functional receptor for the SARS coronavirus. *Nature.* 426, 450-454
54. Wrapp, et al., (2020) Cryo-EM structure of the 2019-nCoV spike in the prefusion conformation. *Science.* 367, 1260-1263
55. Yan, R., Zhang, Y., Li, Y., Xia, L., Guo, Y., and Zhou, Q. (2020) Structural basis for the recognition of SARS-CoV-2 by full-length human ACE2. *Science.* 367, 1444-1448
56. Li, F. (2016) Structure, Function, and Evolution of Coronavirus Spike Proteins. *Annual Review of Virology.* 3, 237-261
57. Zhang, et al., (2020) Site-specific N-glycosylation Characterization of Recombinant SARS-CoV-2 Spike Proteins using High-Resolution Mass Spectrometry. *bioRxiv.* 10.1101/2020.03.28.013276
58. Bosch, et al., (2004) Severe acute respiratory syndrome coronavirus (SARS-CoV) infection inhibition using spike protein heptad repeat-derived peptides. *PNAS.* 101, 8455-8460
59. Walls, et al., (2019) Unexpected Receptor Functional Mimicry Elucidates Activation of Coronavirus Fusion. *Cell.* 176, 1026-1039.e15
60. Wei, X., Decker, J. M., Wang, S., Hui, H., Kappes, J. C., Wu, X., Salazar-Gonzalez, J. F., Salazar, M. G., Kilby, J. M., Saag, M. S., Komarova, N. L., Nowak, M. A., Hahn, B. H., Kwong, P. D., and Shaw, G. M. (2003) Antibody neutralization and escape by HIV-1. *Nature.* 422, 307-312
61. Wu, N. C., and Wilson, I. A. (2017) A Perspective on the Structural and Functional Constraints for Immune Evasion: Insights from Influenza Virus. *J. Mol. Biol.* 429, 2694-2709
62. Watanabe, Y., Raghwani, J., Allen, J. D., Seabright, G. E., Li, S., Moser, F., Huiskonen, J. T., Strecker, T., Bowden, T. A., and Crispin, M. (2018) Structure of the Lassa virus glycan shield provides a model for immunological resistance. *PNAS.* 115, 7320-7325
63. Datema, R., Romero, P. A., Rott, R., and Schwarz, R. T. (1984) On the role of oligosaccharide trimming in the maturation of sindbis and influenza virus. *Archives of Virology.* 81, 25-39
64. Qu, et al., (2011) Inhibitors of Endoplasmic Reticulum α-Glucosidases Potently Suppress Hepatitis C Virus Virion Assembly and Release. *Antimicrobial Agents and Chemotherapy.* 55, 1036-1044
65. Chang, et al., (2009) Novel Imino Sugar Derivatives Demonstrate Potent Antiviral Activity against Flaviviruses. *Antimicrobial Agents and Chemotherapy.* 53, 1501-1508
66. Block, et al., (1994) Secretion of human hepatitis B virus is inhibited by the imino sugar N-butyldeoxynojirimycin. *Proc Natl Acad Sci USA.* 91, 2235-2239
67. Block, T. M., and Jordan, R. (2001) Iminosugars as possible broad spectrum anti hepatitis virus agents: the glucovirs and alkovirs. *Antivir. Chem. Chemother.* 12, 317-325
68. Vincent, et al., (2005) Chloroquine is a potent inhibitor of SARS coronavirus infection and spread. *Virol J.* 10.1186/1743-422X-2-69
69. Savarino, et al., (2006) New insights into the antiviral effects of chloroquine. *The Lancet Infectious Diseases.* 6, 67-69
70. Suzuki, T. (2015) The cytoplasmic peptide:N-glycanase (Ngly1)—basic science encounters a human genetic disorder. *Journal of Biochemistry.* 157, 23-34
71. Huang, Y., and Orlando, R. (2017) Kinetics of N-Glycan Release from Human Immunoglobulin G (IgG) by PNGase F: All Glycans Are Not Created Equal. *J Biomol Tech.* 28, 150-157

72. Kuhn, P., Guan, C., Cui, T., Tarentino, A. L., Plummer, T. H., and Roey, P. V. (1995) Active Site and Oligosaccharide Recognition Residues of Peptide-N4-(N-acetyl-β-D-glucosaminyl)asparagine Amidase F. *J. Biol. Chem.* 270, 29493-29497

73. Ftouhi-Paquin, et al., (1997) Molecular Cloning, Primary Structure, and Properties of a New Glycoamidase from the Fungus Aspergillus tubigensis. *J. Biol. Chem.* 272, 22960-22965

74. Hirsch, C., Blom, D., and Ploegh, H. L. (2003) A role for N-glycanase in the cytosolic turnover of glycoproteins. *EMBO J.* 22, 1036-1046

75. Suzuki, et al., (2000) PNG1, a yeast gene encoding a highly conserved peptide:N-glycanase. *J. Cell Biol.* 149, 1039-1052

76. Wiertz, et al., (1996) Sec61-mediated transfer of a membrane protein from the endoplasmic reticulum to the proteasome for destruction. *Nature.* 384, 432-438

77. Hughes, E. A., Hammond, C., and Cresswell, P. (1997) Misfolded major histocompatibility complex class I heavy chains are translocated into the cytoplasm and degraded by the proteasome. *Proc. Natl. Acad. Sci. U.S.A.* 94, 1896-1901

78. Zhao, et al., (2009) Structural and mutational studies on the importance of oligosaccharide binding for the activity of yeast PNGase. *Glycobiology.* 19, 118-125

79. Lee, et al., (2005) Structure of a peptide:N-glycanase-Rad23 complex: insight into the deglycosylation for denatured glycoproteins. *Proc. Natl. Acad. Sci. U.S.A.* 102, 9144-9149

80. Makarova, et al., (1999) A superfamily of archaeal, bacterial, and eukaryotic proteins homologous to animal transglutaminases. *Protein Science.* 8, 1714-1719

81. Katiyar, et al., (2002) Site-directed mutagenesis study of yeast peptide:N-glycanase. Insight into the reaction mechanism of deglycosylation. *J. Biol. Chem.* 277, 12953-12959

82. Zhao, et al., (2006) Structure of the Mouse Peptide N-Glycanase-HR23 Complex Suggests Co-evolution of the Endoplasmic Reticulum-associated Degradation and DNA Repair Pathways. *J. Biol. Chem.* 281, 13751-13761

83. Zhou, et al., (2006) Structural and biochemical studies of the C-terminal domain of mouse peptide-N-glycanase identify it as a mannose-binding module. *Proc. Natl. Acad. Sci. U.S.A.* 103, 17214-17219

84. Suzuki, T., Park, H., Till, E. A., and Lennarz, W. J. (2001) The PUB domain: a putative protein-protein interaction domain implicated in the ubiquitin-proteasome pathway. *Biochem. Biophys. Res. Commun.* 287, 1083-1087

85. Park, H., Suzuki, T., and Lennarz, W. J. (2001) Identification of proteins that interact with mammalian peptide:N-glycanase and implicate this hydrolase in the proteasome-dependent pathway for protein degradation. *Proc. Natl. Acad. Sci. U.S.A.* 98, 11163-11168

86. KOBATA, A. (2013) Exo- and endoglycosidases revisited. *Proc Jpn Acad Ser B Phys Biol Sci.* 89, 97-117

87. Vulnerabilities in coronavirus glycan shields despite extensive glycosylation | bioRxiv [online] https://www.biorxiv.org/content/10.1101/2020.02.20.957472v1 (Accessed May 19, 2020)

88. Yang, et al., (2015) The I-TASSER Suite: protein structure and function prediction. *Nat. Methods.* 12, 7-8

89. Roy, et al., (2010) I-TASSER: a unified platform for automated protein structure and function prediction. *Nature Protocols.* 5, 725-738

90. Zhang, Y. (2008) I-TASSER server for protein 3D structure prediction. *BMC Bioinformatics.* 9, 40

91. GLYCAM-Web | Utilities for molecular modeling of carbohydrates [online] https://dev.glycam.org/ (Accessed Jun. 5, 2020)

92. Calas, et al., (2017) The importance of simulated lung fluid (SLF) extractions for a more relevant evaluation of the oxidative potential of particulate matter. *Scientific Reports.* 7,11617

93. Song, et al., (2004) Synthesis and Characterization of a Native, Oligomeric Form of Recombinant Severe Acute Respiratory Syndrome Coronavirus Spike Glycoprotein. *Journal of Virology.* 78, 10328-10335

94. Juarez, et al., (2011) The Role and Specificity of the Catalytic and Regulatory Cation-binding Sites of the Na+-pumping NADH:Quinone Oxidoreductase from Vibrio cholerae. *J. Biol. Chem.* 286, 26383-26390

95. Juárez, et al., (2010) Energy transducing redox steps of the Na+-pumping NADH:quinone oxidoreductase from Vibrio cholerae. *Proc. Natl. Acad. Sci. U.S.A.* 107, 12505-12510

96. Juárez, O., Athearn, K., Gillespie, P., and Barquera, B. (2009) Acid residues in the transmembrane helices of the Na+-pumping NADH:quinone oxidoreductase from Vibrio cholerae involved in sodium translocation. *Biochemistry.* 48, 9516-9524

97. Ren, et al., (2006) Analysis of ACE2 in polarized epithelial cells: surface expression and function as receptor for severe acute respiratory syndrome-associated coronavirus. *Journal of General Virology,.* 87, 1691-1695

98. Matsuyama, et al., (2020) Enhanced isolation of SARS-CoV-2 by TMPRSS2-expressing cells. *PNAS.* 117, 7001-7003

99. Kitajima, et al., (1995) Identification and distribution of peptide:N-glycanase (PNGase) in mouse organs. *Arch. Biochem. Biophys.* 319, 393-401

100. Suzuki, et al., (2003) Ngly1, a mouse gene encoding a deglycosylating enzyme implicated in proteasomal degradation: expression, genomic organization, and chromosomal mapping. *Biochemical and Biophysical Research Communications.* 304, 326-332

101. Raran-Kurussi, et al., (2017) Removal of Affinity Tags with TEV Protease. *Methods Mol. Biol.* 1586, 221-230

102. Wu, et al., (2012) Removal of the Tag from His-tagged ILYd4, a Human CD59 Inhibitor, Significantly Improves its Physical Properties and its Activity. *Curr Pharm Des.* 18, 4187-4196

103. Wang, et al., (2019) Development of a colorimetric PNGase activity assay. *Carbohydr. Res.* 472, 58-64

104. Fang, et al., (2019) Conserved residue His-257 of Vibrio cholerae flavin transferase ApbE plays a critical role in substrate binding and catalysis. *J. Biol. Chem.* 294, 13800-13810

105. Rosenbaum, et al., (2006) The Structural Biology Center 19ID undulator beamline: facility specifications and protein crystallographic results. *J Synchrotron Radiat.* 13, 30-45

106. Minor, et al., (2006) HKL-3000: the integration of data reduction and structure solution—from diffraction images to an initial model in minutes. *Acta Crystallogr. D Biol. Crystallogr.* 62, 859-866

107. Vagin, A., and Teplyakov, A. (1997) MOLREP: an Automated Program for Molecular Replacement. *J Appl Cryst.* 30, 1022-1025

108. Terwilliger, T. (2004) SOLVE and RESOLVE: automated structure solution, density modification and model building. *J Synchrotron Radiat.* 11, 49-52

109. Morris, R. J., Perrakis, A., and Lamzin, V. S. (2003) ARP/wARP and automatic interpretation of protein electron density maps. *Meth. Enzymol.* 374, 229-244
110. Emsley, P., and Cowtan, K. (2004) Coot: model-building tools for molecular graphics. *Acta Crystallogr. D Biol. Crystallogr.* 60, 2126-2132
111. Murshudov, G. N., Vagin, A. A., and Dodson, E. J. (1997) Refinement of macromolecular structures by the maximum-likelihood method. *Acta Crystallogr. D Biol. Crystallogr.* 53, 240-255
112. Collaborative Computational Project, Number 4 (1994) The CCP4 suite: programs for protein crystallography. *Acta Crystallogr. D Biol. Crystallogr.* 50, 760-763
113. Adams, et al., (2002) PHENIX: building new software for automated crystallographic structure determination. *Acta Crystallogr. D Biol. Crystallogr.* 58, 1948-1954
114. Davis, et al., (2004) MOLPROBITY: structure validation and all-atom contact analysis for nucleic acids and their complexes. *Nucleic Acids Res.* 32, W615-619
115. Harcourt, et al., Early Release—Severe Acute Respiratory Syndrome Coronavirus 2 from Patient with Coronavirus Disease, United States—Volume 26, Number 6—June 2020—Emerging Infectious Diseases journal—CDC. 10.3201/eid2606.200516
116. Sims, et al., (2005) Severe Acute Respiratory Syndrome Coronavirus Infection of Human Ciliated Airway Epithelia: Role of Ciliated Cells in Viral Spread in the Conducting Airways of the Lungs. *J Virol.* 79, 15511-15524
117. Mast, et al., (2006) Family 47 α-Mannosidases in N-Glycan Processing. *Methods Enzymol.* 415, 31-46
118. Winchester, B. (1984) Role of alpha-D-mannosidases in the biosynthesis and catabolism of glycoproteins. *Biochem. Soc. Trans.* 12, 522-524
119. Andersson, et al., (2005) Sequencing, expression, and enzymatic characterization of β-hexosaminidase in rabbit lacrimal gland and primary cultured acinar cells. *Glycobiology.* 15, 211-220
120. You, J., Lin, S., and Jiang, T. (2019) Origins and Evolution of the α-L-Fucosidases: From Bacteria to Metazoans. *Front. Microbiol.* 10.3389/fmicb.2019.01756
121. Shang, et al., (2020) Structural basis of receptor recognition by SARS-CoV-2. *Nature.* 581, 221-224
122. Chakraborti, et al., (2005) The SARS Coronavirus S Glycoprotein Receptor Binding Domain: Fine Mapping and Functional Characterization. *Virology Journal.* 2, 73
123. Chen, Y., Guo, Y., Pan, Y., and Zhao, Z. J. (2020) Structure analysis of the receptor binding of 2019-nCoV. *Biochemical and Biophysical Research Communications.* 525, 135-140
124. Wang, et al., (2020) Structural and Functional Basis of SARS-CoV-2 Entry by Using Human ACE2. *Cell.* 181, 894-904.e9
125. Altmann, et al., (1995) Kinetic comparison of peptide: N-glycosidases F and A reveals several differences in substrate specificity. *Glycoconjugate J.* 12, 84-93
126. Willow, S. Y., Bing, X., Lawrence, J., Eisenberg, R. S., and Minh, D. D. L. (2020) On the Polarization of Ligands by Proteins. *Physical Chemistry Chemical Physics.* 10.1039/d0cp00376j
127. Du, Y et al., (2015) Rapid Sample Preparation Methodology for Plant N-Glycan Analysis Using Acid-Stable PNGase H+. *J. Agric. Food Chem.* 63, 10550-10555
128. Kim, et al., (2019) Generation of a Nebulizable CDR-Modified MERS-CoV Neutralizing Human Antibody. *Int. J. Mol. Sci.* 20, 5073
129. Zhao, et al., (2007) Studies on peptide:N-glycanase-p97 interaction suggest that p97 phosphorylation modulates endoplasmic reticulum-associated degradation. *Proceedings of the National Academy of Sciences.* 104, 8785-8790
130. Chennamsetty, et al., (2009) Design of therapeutic proteins with enhanced stability. *Proceedings of the National Academy of Sciences.* 106, 11937-11942
131. Onufriev, A. V., and Case, D. A. (2019) Generalized Born Implicit Solvent Models for Biomolecules. *Annu. Rev. Biophys.* 48, 275-296
132. Lipparini, F et al., (2014) Quantum, classical, and hybrid QM/MM calculations in solution: General implementation of the ddCOSMO linear scaling strategy. *J. Chem. Phys.* 141, 184108
133. Seeliger, D., and de Groot, B. L. (2010) Protein Thermostability Calculations Using Alchemical Free Energy Simulations. *Biophysical Journal.* 98, 2309-2316

What is claimed is:

1. A pharmaceutical formulation for inactivating a virus having fully or partially glycosylated surface glycoproteins, the pharmaceutical formulation comprising an active portion of a glycosidase and a pharmaceutically acceptable carrier configured to deliver the active portion to an infecting virus within an infected human or animal, wherein the active portion retains enzymatic activity and is adapted to remove glycans from the surface glycoproteins.

2. A pharmaceutical formulation of claim 1, wherein the glycosidase is selected from the group consisting of endo- and exo-glycosidases, including: peptide N-glycosidase (PNGase), endo-beta-N-acetylglucosaminidase (ENGase), fucosidase, mannosidase, sialidase, alpha- or beta-galactosidase, neuraminidase, hexosaminidase, aspartyl-glucosaminidase and combinations thereof.

3. The pharmaceutical formulation of claim 1, wherein the active portion of the glycosidase is bound to a binding domain corresponding to the surface glycoprotein of the virus.

4. The pharmaceutical formulation of claim 3, further comprising a connecting domain connecting the active portion and the binding domain.

5. A fusion protein comprising:

a catalytic domain of a glycosidase, wherein the catalytic domain of the glycosidase has activity to remove glycans from a targeted virus infecting a human or an animal;

a binding domain of a protein receptor configured to bind to the targeted virus; and a connecting domain connecting the catalytic domain to the binding domain of the protein receptor.

6. The fusion protein of claim 5, wherein the protein receptor is an angiotensin converting enzyme 2 (ACE2) receptor.

7. The fusion protein of claim 6, wherein said catalytic domain is substantially similar to a peptide domain selected from the group consisting of endo- and exo-glycosidases, including: peptide N-glycosidase (PNGase), endo-beta-N-acetylglucosaminidase (ENGase), fucosidase, mannosidase, sialidase, alpha- or beta-galactosidase, neuraminidase, hexosaminidase, aspartyl-glucosaminidase and combinations thereof.

8. The fusion protein of claim 7, wherein the catalytic domain has at least 50% sequence identity with the peptide domain.

9. The fusion protein of claim 7, wherein said catalytic domain further comprises an affinity-enhancing domain, which is configured to bind tightly to complex glycans and enhance a catalytic effect of the catalytic domain.

10. The fusion protein of claim 6, wherein the ACE2 receptor is substantially similar to human ACE2 receptor.

11. The fusion protein of claim 6, wherein the connecting domain comprises a flexible loop of 5-20 amino acid residues.

12. A pharmaceutical formulation comprising the fusion protein of claim 5.

13. The pharmaceutical formulation of claim 12 in formulation as an inhalant.

14. A method for treating or preventing viral infection by a coronavirus or other viruses having a fully or partially glycosylated surface glycoprotein, the method comprising: applying a therapeutically effective amount of the formulation of claim 11 to epithelial cells of a human or an animal.

15. The method of claim 14, wherein the coronavirus is SARS-CoV-2 virus.

16. The method of claim 14, wherein the applying the effective amount of the formulation comprises inhaling the formulation by the subject.

17. The method of claim 14, wherein the epithelial cells are respiratory epithelial cells.

* * * * *